(12) United States Patent
Guinez et al.

(10) Patent No.: US 6,770,292 B2
(45) Date of Patent: Aug. 3, 2004

(54) PHARMACEUTICAL COMPOSITIONS FOR ORAL ADMINISTRATION

(75) Inventors: Charles Guinez, Bordeaux (FR); René Laversanne, Pessac (FR); Joëlle Amedee, Pessac (FR)

(73) Assignee: Capsules, Pessac (FR)

( * ) Notice: Subject to any disclaimer, the term of this patent is extended or adjusted under 35 U.S.C. 154(b) by 52 days.

(21) Appl. No.: 10/149,428

(22) PCT Filed: Dec. 27, 2000

(86) PCT No.: PCT/FR00/03692

§ 371 (c)(1),
(2), (4) Date: Jun. 24, 2002

(87) PCT Pub. No.: WO01/49264

PCT Pub. Date: Jul. 12, 2001

(65) Prior Publication Data

US 2003/0072797 A1 Apr. 17, 2003

(30) Foreign Application Priority Data

Jan. 3, 2000 (FR) .......................................... 00 00015

(51) Int. Cl.$^7$ ............................................... A61K 38/00
(52) U.S. Cl. ........................ 424/450; 514/808; 514/54; 514/56; 530/307; 424/401
(58) Field of Search ................................. 424/450, 401, 424/400, 434, 464, 45, 46, 184.1, 725; 514/808, 56, 2; 530/307

(56) References Cited

U.S. PATENT DOCUMENTS 6,290,987 B1 * 9/2001 Modi

FOREIGN PATENT DOCUMENTS

WO 93/19737 10/1993

* cited by examiner

Primary Examiner—Christopher R. Tate
Assistant Examiner—B. Dell Chism
(74) Attorney, Agent, or Firm—Dennison, Schultz, Dougherty & MacDonald (57) ABSTRACT

A method for oral administration of an active principle includes the steps of incorporating an active principle in multilamellar vesicles having a diameter of between 0.1 and 25 μm, and a lamellar liquid-crystal internal structure formed, from the center to the periphery of the vesicles, of a stack of concentric bilayers based on amphiphilic agents alternating with layers of water, aqueous solution or solution of a polar liquid, and orally administering a composition containing the active principle incorporated within the vesicles.

19 Claims, 3 Drawing Sheets

PHARMACEUTICAL COMPOSITIONS FOR ORAL ADMINISTRATION

BACKGROUND OF THE INVENTION

The present invention relates to novel pharmaceutical compositions for oral administration.

Nowadays a large number of drugs need to be administered parenterally, either by intramuscular, subcutaneous or intravenous injection or by incorporation into a perfusion. In general, such a route of administration is necessitated by:

fragility of the active molecule under the physicochemical and biological conditions of the gastrointestinal tract (pH, enzymes, etc.), non-permeability of the gastrointestinal barrier to the active molecule, toxicity or excessive irritative capacity of the active molecule towards the gastro-intestinal mucosa.

The following may be mentioned as examples of molecules which fall in the category of those which have to be administered parenterally:

peptides and polypeptides, particularly hormones, which are decomposed by the gastrointestinal media, heparin, which does not pass through the barrier, numerous cytostatics, which are known for their toxicity and for the non-permeability of the gastrointestinal barrier thereto.

Furthermore, other mucous tissues which could be preferred drug administration sites are not used as such because of their low permeability to the active molecules in question. This sometimes makes it necessary to use either systemic administration or a strong overdose of the active principle. In both cases, the dose administered is considerably greater than the dose required, which causes numerous disadvantages in terms of cost as well as drug safety.

In addition, the patient's acceptance of the treatment and the patient's comfort are parameters which are increasingly being taken into account in the development of novel drugs. Non-invasive, oral administration therefore represents a distinct advance in this respect.

Several approaches have been developed to facilitate the oral administration of drugs.

The most classical approach, aimed at protecting the active principle from the acidity and enzymatic action encountered in the stomach, consists in coating the active molecule in a tablet whose outer film is resistant to such a medium. In general, said coating dissolves once it is placed under neutral pH conditions such as those encountered in the intestine, thus allowing the release of the active ingredient. This approach is effective for molecules which either act directly in the intestine or have no difficulty in passing into the general circulation through the intestinal mucosa. It is not therefore effective for promoting the transmembrane transport necessary for certain molecules like heparin, nor is it applicable to molecules sensitive to the enzymes present in the intestine (particularly proteases, which destroy proteins).

Derived from this technology, microcapsules coated with polymers make it possible not only to protect the active principle but also to release it in a controlled or delayed manner in the intestine and hence to improve the pharmacokinetics, thereby affording e.g. a reduction in the side effects of the product. Such an invention is described in European patent EP 0 709 087 in the name of Flamel. The particle diameter (in the order of a few hundred to a few thousand micrometers) and the coating thickness can be modified, allowing variations in the kinetic release profiles.

Numerous tests have employed different technologies based on microvesicles or on microspheres or nanospheres of polymers for the purpose of protecting the active principle, but also of facilitating its passage through the gastrointestinal membrane into the bloodstream. There may be mentioned liposomes (cf. M. Ueno et al., Chem. Pharm. Bull., 30 pp. 2245–2247, 1982) used to facilitate the passage of heparin, or polyalkyl cyanoacrylate nanospheres used for the oral administration of insulin (C. Damgé et al., J. Pharma. Sc., 86 pp. 1403–1409, 1997). Based on another technology, adjuvants such as acetylated derivatives of amino acids (A. Leone-Bay et al., J. Controlled Release, 50 pp. 41–49, 1998) or hydrogels (J. M. Dunn & A. S. Hollister, Current Therap. Res., 56 pp. 738–745, 1995) have been used to facilitate the oral administration of heparin.

As regards vesicles, i.e. spherical objects formed of molecular arrangements of amphiphilic molecules, multilamellar vesicles have formed the subject of important researches and have given rise to several applications. Examples which may be mentioned are international patent applications WO 93/19735, WO 95/18601, WO 97/00623, WO 98/02144 and WO 99/16468. Such vesicles, which are referred to in the above-cited documents as multilamellar vesicles with an onion structure, differ from liposomes by:

their method of preparation, which starts from a lamellar liquid-crystal phase, i.e. a phase at thermodynamic equilibrium with a long-range order;

their lamellar liquid-crystal internal structure. This structure is formed of a stack of concentric bilayers of amphiphiles alternating with layers of water, aqueous solution or solution of a polar liquid (e.g. glycerol) from the center to the periphery of these vesicles. Before their dispersion in a use medium, these vesicles are in a state of thermodynamic equilibrium. The specific structure of these vesicles can easily be demonstrated by optical microscopy, particularly polarizing optical microscopy;

the varied nature of the amphiphilic molecules which can be used, by themselves or in a mixture, to form the vesicles;

the media in which the vesicles can be dispersed, which can be hydrophilic or lipophilic depending on the formulation.

The size of these multilamellar vesicles is in the order of a micrometer, the diameter typically being from 0.1 $\mu$m to 20 $\mu$m. Their use for the oral administration of a drug has never been illustrated or demonstrated.

SUMMARY OF THE INVENTION

The inventors of the present invention have now discovered that the oral administration of multilamellar vesicles having the specific structure defined above, incorporating a molecule known for its inability to be administered by this route, either because of its fragility or because of its inability to pass through the gastro-intestinal barrier, is made possible when said molecule is incorporated in these multilamellar vesicles. Incorporating the molecule in this way favors its passage through the gastrointestinal wall and enables it to enter the bloodstream. This discovery was made on the basis of experiments conducted on molecules of very different natures and characteristics, such as heparin on the one hand and calcitonin on the other.

One advantage of the invention is that these multilamellar vesicles are prepared from biocompatible constituents known for their harmlessness.

Another advantage of the invention is that the process for the preparation of vesicles is simple to carry out and only calls for standard chemical apparatus.

Furthermore, the fact that the process involves an initial lamellar phase at thermodynamic equilibrium gives it an excellent reproducibility and gives the resulting vesicles a high stability.

DETAILED DESCRIPTION OF THE INVENTION

Thus, according to one of its essential characteristics, the invention relates to the use of multilamellar vesicles having a lamellar liquid-crystal internal structure formed, from the center to the periphery of said vesicles, of a stack of concentric bilayers based on amphiphilic agents alternating with layers of water, aqueous solution or solution of a polar liquid, with at least one active principle being incorporated inside said vesicles, for the manufacture of a pharmaceutical composition for oral administration.

The term "incorporated", which we use in preference to the term "encapsulated", is to be understood as meaning that the active principle or principles form an integral part of the entity consisting of the vesicle. In fact, molecules of active principle can be found in any layer between the center and the periphery of said vesicle.

The expression "oral administration" is used in its normal sense and means that the product is introduced into the organism through the mouth, as opposed to a parenteral mode of administration, for example.

It became apparent, during the tests performed by the inventors, that the incorporation of an active principle into vesicles offered various advantages already explained above. In particular, vesicles act as true vectors for the active principle, making it possible to facilitate its passage through the gastrointestinal barrier and/or to protect it from degradation, particularly degradation by the enzymes present in the gastrointestinal medium.

The vesicles used generally have diameters of between 0.1 and 25 µm, preferably of between 0.2 and 15 µm.

More precisely, the vesicles used according to the invention preferably consist of several layers of amphiphilic agents alternating with layers of aqueous or polar phase. The thickness of each of these layers is a molecular thickness, typically in the order of 5 to 10 nanometers. Therefore, for a stack of about ten to a few hundred layers, a diameter of between 0.1 µm and a few tens of micrometers is obtained. This is what is found experimentally, the vesicles being observable by optical microscopy (in polarized light so as to have a better contrast associated with their birefringence), either as unresolved dots in the case of the smallest vesicles, or as birefringent spheres in the case of the largest vesicles. The size profile can be studied with a laser granulometer (utilizing the static scattering of a laser beam, analyzed at several angles). A gaussian profile centered on a value varying between 0.1 and 25 µm, showing a slight heterogeneity of size for a given formulation, is generally obtained under given preparative conditions.

As explained above, the vesicles in which the active agent is incorporated have a multilamellar so-called onion structure and consist, from their center to their periphery, of a series of lamellar layers separated by a liquid medium. These vesicles can be obtained by a process comprising the preparation of a lamellar liquid-crystal phase and its transformation by the application of shear. Such a process is described in particular in patent WO 93/19735, derived from French patent FR 2 689 418, or in patent WO 95/18601, which are introduced here by way of reference.

In French patent FR 2 689 418 this transformation can be performed in a step involving homogeneous shear of the liquid-crystal phase, which produces vesicles, also called microcapsules, of controlled size. However, by varying the formulation of the lamellar liquid-crystal phase, particularly the nature of the surfactants included in its composition, the transformation of this liquid-crystal phase to vesicles can be effected simply by means of mechanical stress, particularly when the constituents are mixed.

Inter alia, such vesicles have the advantage of being able to be prepared by a particularly simple preparative process which allows a wide variety of surfactants to be used.

Another advantage, again associated essentially with the process used to prepare the vesicles of so-called onion structure used according to the invention, lies in the fact that the active agents and the additives are incorporated prior to the formation of the vesicles; this affords an excellent encapsulation yield and hence a greater efficiency and a very substantial saving in the case of expensive molecules.

Such structures are advantageously obtained by the incorporation of at least one active agent into a lamellar liquid-crystal phase comprising at least one surfactant, followed by transformation of this lamellar liquid-crystal phase to a dense phase of small multilamellar vesicles.

It is important to note that this transformation does not modify the liquid-crystal symmetry of the initial phase which characterizes the multilamellar vesicles. This liquid-crystal symmetry is evident from macroscopic observations, such as birefringence in optical microscopy, or the presence of a diffraction peak in X-ray analysis. It should be pointed out, however, that such observations can be made difficult either by the poor contrast associated with the very small size of the vesicles in optical microscopy, or by the dilution and hence the weakness of the signal in X-ray diffraction.

Thus the vesicles used according to the invention can be obtained by a process in which a lamellar liquid-crystal phase incorporating at least one active agent is prepared and said liquid-crystal phase is caused to rearrange into multilamellar vesicles by the application of shear or mechanical stress resulting e.g. from the mixing of the constituents of said lamellar liquid-crystal phase.

This shear may be homogeneous shear, which has the advantage of producing vesicles of perfectly homogeneous size. However, simple mechanical agitation may prove sufficient for forming the multilamellar vesicles of the invention.

Although this is not obligatory, the amphiphilic molecules used to prepare the vesicles will be selected from molecules described in the pharmacopeia or molecules already used in drugs for oral administration. The following group may be mentioned, although the list is not exhaustive and the products have not necessarily been used previously in pharmacy:

- hydrogenated or non-hydrogenated glycerolipids, particularly phospholipids,
- ethoxylated or non-ethoxylated, linear or branched, saturated or mono- or polyunsaturated $C_6$ to $C_{30}$ fatty acids in the form of the acid or an alkali metal, alkaline earth metal or amine salt,
- ethoxylated or non-ethoxylated esters of sucrose, sorbitol, mannitol, glycerol or polyglycerol containing from 2 to 20 glycerol units, or glycol with the above fatty acids,
- mono-, di- or triglycerides or mixtures of glycerides of the above fatty acids,
- ethoxylated or non-ethoxylated, linear or branched, saturated or mono- or polyunsaturated $C_6$ to $C_{30}$ fatty alcohols,
- cholesterol and derivatives thereof, particularly charged or neutral cholesterol esters such as cholesterol sulfate,
- other derivatives with a sterol skeleton, particularly those of vegetable origin such as sitosterol or sigmasterol,
- ethoxylated or non-ethoxylated ethers of sucrose, sorbitol, mannitol, glycerol or polyglycerol containing from 2 to 20 glycerol units, or glycol with the above fatty alcohols,
- hydrogenated or non-hydrogenated, polyethoxylated vegetable oils,
- polyoxyethylene/polyoxypropylene block polymers (poloxamers),
- polyethylene glycol hydroxystearate,
- sphingolipids and sphingosine derivatives,
- polyalkyl glucosides,
- ceramides,
- polyethylene glycol/alkyl glycol copolymers, for example the copolymers of the ELFACOS family from AKZO NOBEL,
- polyethylene glycol/polyalkylene glycol ether di-block or tri-block copolymers, for example the copolymers of the ARLACELL family from ICI.

These amphiphiles or surfactants can be used by themselves or in a mixture. Some of these amphiphiles are capable on their own of forming a lamellar liquid-crystal phase by being mixed with a polar solvent. Others are used solely in a mixture, in a lower proportion, to confer rigidity or impermeability properties on the lamellar liquid-crystal phase.

The formulation advantageously comprises a mixture of surface-active molecules. In general, at least two different surfactants having different hydrophilic-lipophilic balances are used, which makes it possible continuously to adjust the properties of the bilayers and thus to control the appearance of the instability governing the formation of the multilamellar vesicles.

Thus, from the above surfactants, it will be advantageous to choose two which have relatively different properties, in particular a different hydrophilic-lipophilic balance (HLB). The first surfactant will advantageously have a hydrophilic-lipophilic balance of between 1 and 6, preferably of between 1 and 4, while the second surfactant will have a hydrophilic-lipophilic balance of between 3 and 15, preferably of between 5 and 15.

Another advantage of the vesicles used according to the invention is that natural or artificial polymers, such as polysaccharides (alginates, chitosan, etc.), can be added to the formulation in order to increase the strength of the vesicle and enable it better to withstand the physicochemical stresses of the administration medium (pH, mechanical effect, osmotic pressure, etc.). These polymers can either be incorporated into the vesicle or deposited around it in the form of a coating. In the latter case, the vesicle or the particle formed of the vesicles coated in the polymer matrix has a larger diameter than the vesicles alone. These polymers can optionally be crosslinked to further increase their strength.

The vesicles used according to the invention advantageously have a diameter of between 0.1 and 25 μm, preferably of between 0.2 and 15 μm.

In the compositions used according to the invention, the vesicles are advantageously dispersed in a pharmaceutically acceptable medium generally consisting of water or a buffer, this medium being identical to or different from that found between the lamellae of the vesicles.

The vesicles according to the invention can also be dispersed in a hydrophobic medium, e.g. an oil, which is acceptable for pharmaceutical use, examples being a vegetable or mineral oil, a synthetic fatty acid ester, squalane or squalene. This can have the advantage of avoiding or limiting the presence of water in the case of an active agent which is hydrolyzable, for example. This dispersion in oil can itself be emulsified in an aqueous medium to give a formulation which is more pleasant to swallow. Because of the presence of the oily intermediate phase, the external continuous medium, for example aqueous medium, is separated from the internal medium of the vesicles, thereby additionally protecting the active agent incorporated in the vesicles.

According to another of its features, the invention further relates to the process for the preparation of the vesicles and compositions used according to the invention.

In a first step the method of preparation consists in preparing, by mixing, a lamellar liquid-crystal phase incorporating the various constituents. Said phase is obtained simply by mixing the ingredients in an order determined by the operator according to the miscibilities of each of the constituents. It may be necessary to heat certain pasty or solid constituents in order to facilitate their incorporation. In this case the active molecule is preferably added when mixing has ended, so as to avoid subjecting it to an excessively high temperature if it is temperature-sensitive. It is also possible to prepare a mixture of all the constituents, except the active molecule or its aqueous solution, in the form of a stock mixture to be used as required for preparing the lamellar phase. The aqueous solution can contain a variety of constituents for assuring its biological compatibility, particularly buffer mixtures but also several synergistic active molecules. The lamellar phase prepared in this way is then subjected to moderate shear (from 0 to $1000s^{-1}$) for a limited time (from 0 to 60 minutes).

In the majority of cases this shear is obtained directly by the action of the device used for mixing.

In a third step, the sheared lamellar phase is dispersed in a final medium, generally water or a buffer, which is identical to or different from the medium used to prepare the lamellar phase. This dispersion medium can also be a non-aqueous medium which is either polar (glycerol, polyethylene glycol, alkylene glycol, etc.) or hydrophobic (oils, etc.). This dispersion is generally formed at room temperature (20–25° C.) by slowly adding the medium to the lamellar phase, with constant agitation.

A preservative, and optionally other additives for completing the galenical formulation, can be added to the product.

The Examples which follow illustrate the value of the invention very clearly by demonstrating the passage into the bloodstream of heparin previously incorporated into vesicles according to the invention (Example 1)—in simple solution this product does not pass through the gastrointestinal barrier—and of calcitonin also incorporated into vesicles according to the invention—the same product not incorporated into vesicles is unstable in the gastrointestinal medium (cf. Example 2).

Figure 1:
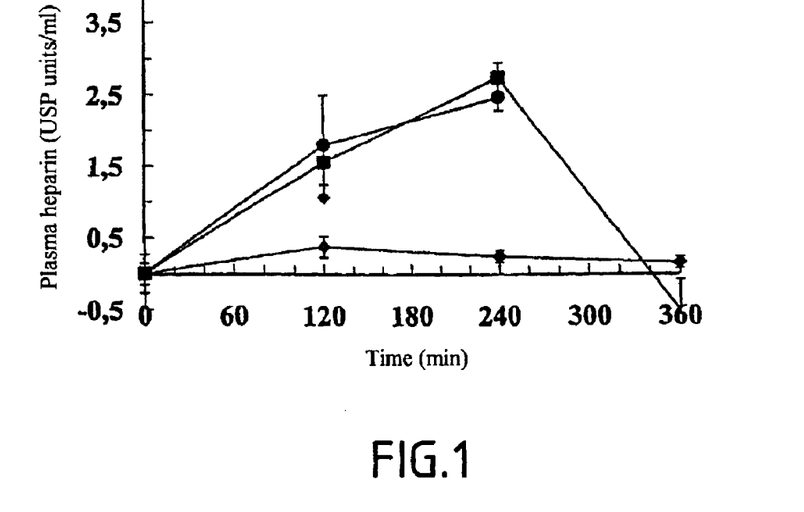
FIGS. 1–3 are graphs of plasma heparin vs. time in rats after oral administration of heparin compositions prepared according to the invention, in comparison with control compositions.
Figure 2:
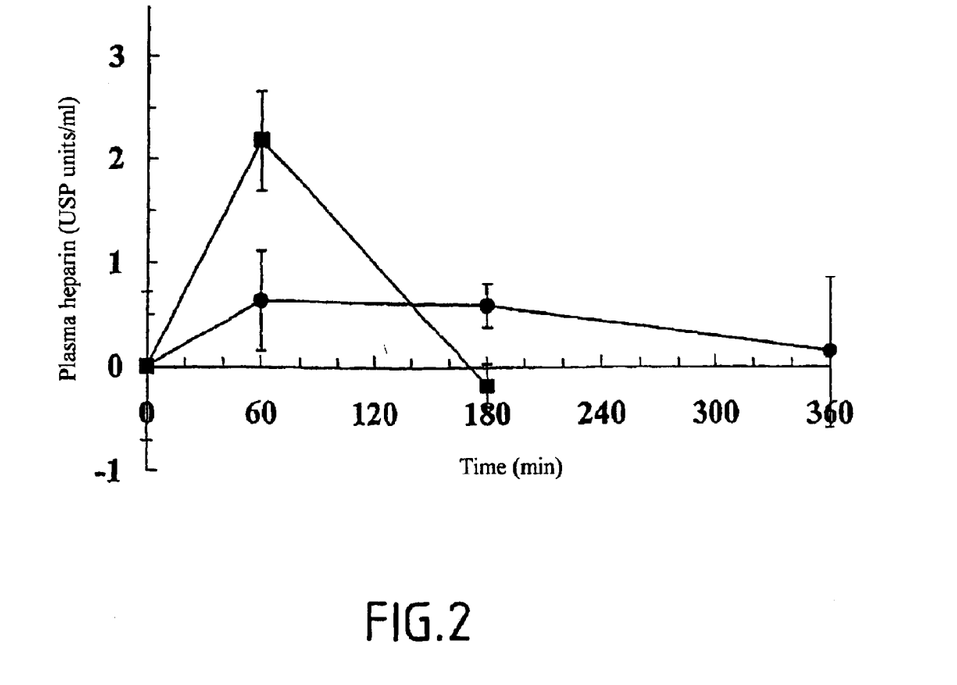
Figure 3:
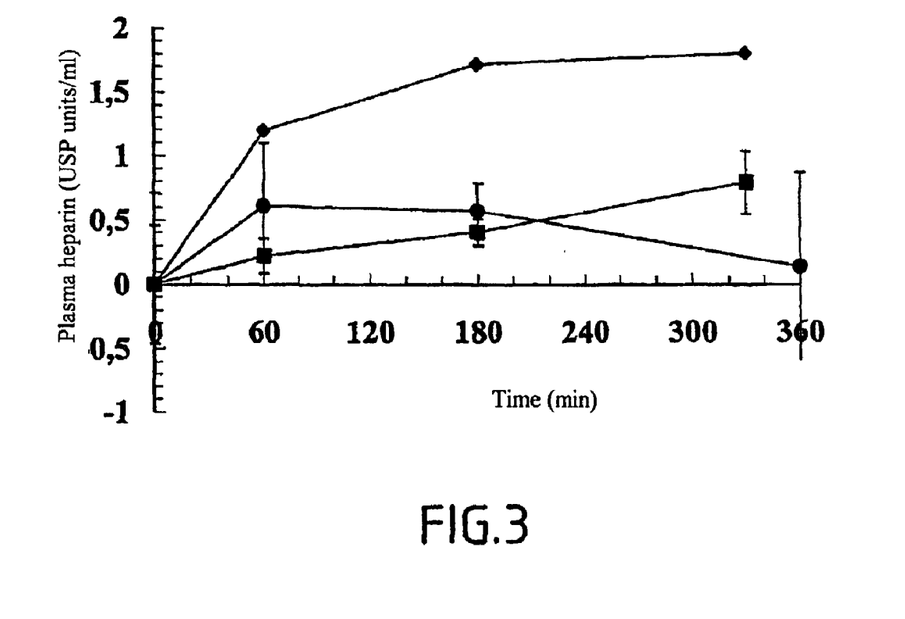
Figure 4:
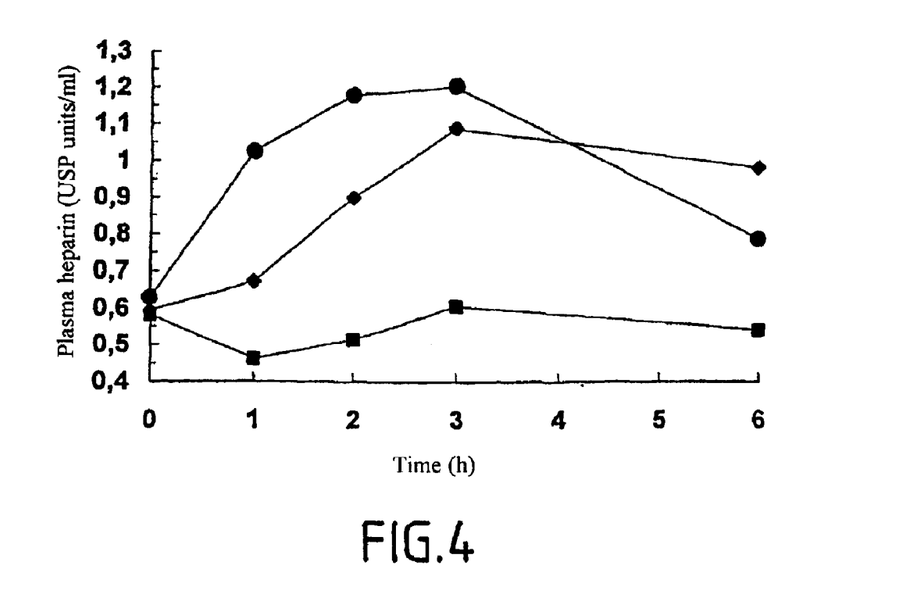
FIG. 4 is a graph of plasma heparin vs. time in dogs after oral administration of a heparin composition prepared according to the invention, in comparison with control compositions.
Figure 5:
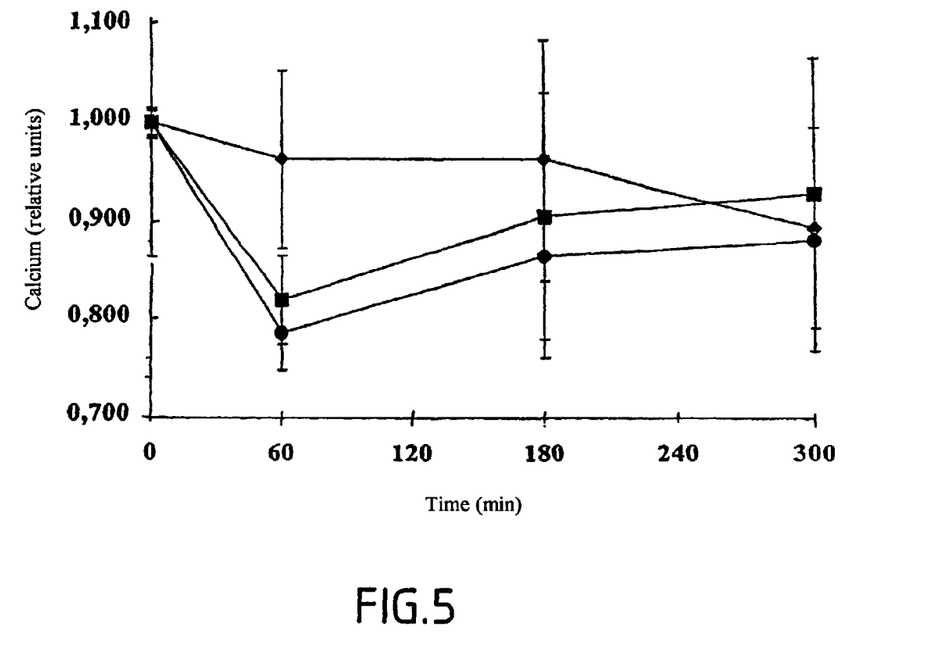
FIG. 5 is a graph of blood calcium vs. time in rats after oral administration of a calcitonin composition according to the invention, in comparison with control compositions.

These Examples are illustrated in FIGS. 1 to 4 for heparin, FIGS. 1 to 3 showing the results of experiments carried out on rats and FIG. 4 showing the results of experiments carried out on dogs, and in FIG. 5 for calcitonin (experiments on rats).

In the Examples which follow, unless indicated otherwise, the proportions given for the constituents of the various formulations are indicated in percentages by weight.

EXAMPLE 1

Vesicles Incorporating Heparin 1.a Formulation and Preparation of Vesicles Incorporating Heparin The heparin used in these Examples is a non-fractionated heparin extracted from pork intestinal mucosa (SIGMA H-9399, 188 USP units/mg).

| Formulation A | |
|---|---|
| ❶ Ethoxylated lauryl alcohol (SEPPIC, Simulsol P4): | 4.0% |
| ❷ Lanolin cholesterol (FLUKA): | 3.0% |
| ❸ Sterile demineralized water: | 10.0% |
| ❹ Heparin at 25% in sterile demineralized water: | 40.0% |
| ❺ Soya lecithin (NATTERMANN, Phospholipon 90): | 43.0% |

Procedure

Constituents ❶, ❷ and ❸ are introduced in any order into a sterile 2 ml pill bottle and then mixed at room temperature with a spatula which has been flame-sterilized beforehand. The total solubilization of constituent ❷ is verified by microscopic observation. Constituent ❹ is then introduced, the mixture is homogenized with the spatula and constituent ❺ is then added.

The whole is homogenized with the spatula and then left to stand overnight at room temperature.

The preparation is then dispersed at a concentration of 16.7% in sterile demineralized water. The heparin titer of the vesicle dispersion is therefore 1.67% (16.7 mg/ml).

| Formulation B | |
|---|---|
| ❶ Ethoxylated lauryl alcohol (SEPPIC, Simulsol P4): | 4.8% |
| ❷ Lanolin cholesterol (FLUKA): | 3.6% |
| ❸ Soya lecithin (NATTERMANN, Phospholipon 90): | 51.6% |
| ❹ 25% solution of heparin in PBS 1x: | 40.0% |

Procedure

Constituents ❶, ❷ and ❸ are introduced in any order into a sterile 2 ml pill bottle and then solubilized in dichloromethane. All the solvent is then evaporated off. Constituent ❹ is added at room temperature. The whole is homogenized with a sterile needle and then dispersed at a concentration of 16.7% in sterile PBS 1x. The heparin titer of the vesicle dispersion is therefore 1.67% (16.7 mg/ml).

| Formulation C | |
|---|---|
| ❶ Ethoxylated lauryl alcohol (SEPPIC, Simulsol P4): | 4.8% |
| ❷ Lanolin cholesterol (FLUKA): | 3.6% |
| ❸ Soya lecithin (NATTERMANN, Phospholipon 90): | 51.6% |
| ❹ 50% solution of heparin in PBS 1x: | 40.0% |

Procedure

Constituents ❶, ❷ and ❸ are introduced in any order into a sterile 2 ml pill bottle and then solubilized in dichloromethane. All the solvent is then evaporated off. Constituent ❹ is added at room temperature. The whole is homogenized with a sterile needle, left to stand overnight at 4° C. and then dispersed at a concentration of 16.7% in sterile PBS 1x. The heparin titer of the vesicle dispersion is therefore 3.34% (33.4 mg/ml).

1.b Physicochemical Characterization of the Vesicles Incorporating Heparin

The vesicles are characterized on the one hand by measurement of the granulometric profile and on the other hand by the encapsulation yield.

Size Profile

The size profile is studied by laser granulometry using a Mastersizer S apparatus from Malvern.

For sample A the size profile shows a main peak centered around 0.34 µm and extending from 50 nm to 20 µm, with a secondary maximum around 6 µm. About 60% (by volume) of the sample has a size below 10 µm.

For sample B the size profile shows a main peak centered around 0.32 µm and extending from 50 nm to 20 µm, with a secondary maximum around 3.5 µm. About 60% (by volume) of the sample has a size below 10 µm.

For sample C the size profile shows a single peak centered around 0.33 µm and extending from 50 nm to 3 µm. About 85% (by volume) of the sample has a size below 1 µm.

The laser scattering analysis is complemented by observation under the polarizing optical microscope, enabling the vesicles to be visualized directly. For samples A and B the observation shows the presence of a very large majority of objects with a size of about a micrometer and a few larger objects. It is also observed that the objects have a tendency to aggregate with one another, but no tendency to coalesce.

Yield of Incorporation in the Vesicles

The incorporation yield is determined by separating the vesicles from their dispersion medium by centrifugation and then analyzing the concentration of heparin in the supernatant. The heparin titer is evaluated by means of a calorimetric test (SIGMA, Heparin Accucolor™ CRS106).

An incorporation yield of 47±5% is obtained for formulation A, meaning that about 50% of the heparin introduced into the sample is inside the vesicles of this formulation A. The incorporation yield measured in the same manner for formulations B and C is 90±5%.

1.c Study of the Administration to Rats of the Vesicles Incorporating Heparin

Administration

The study was carried out on Wistar rats.

The vesicles containing heparin and a negative control solution are administered orally to the non-anesthetized animal by gavage using an intubation needle.

A positive control (aqueous solution of heparin) is injected subcutaneously.

The animals are fasted 24 h before the treatment (water diet). Administration takes place at $T_0$ and blood samples are taken at $T_0$ (before administration) and then at different times thereafter as indicated in the attached Figures.

The doses administered and the protocols are described for each formulation in the Table below:

|  | Formulation A | Formulation B | Formulation C | |
|---|---|---|---|---|
| Rats | 5 male rats of 400 g | 2 male rats of 400 g and 2 female rats of 200 g | 2 male rats of 400 g and 2 female rats of 200 g | |
| Concentration of the dispersion | 16.7 mg/ml | 16.7 mg/ml | 33.4 mg/ml | |
| Dose administered in the vesicles | 2 ml/kg 33.4 mg/kg 6280 USP units/kg | 1.2 ml/kg 20 mg/kg 3760 USP units/kg | Dose I: 0.9 ml/kg 30 mg/kg 5640 USP units/kg | Dose II: 3 ml/kg 100 mg/kg 18,600 USP units/kg |
| Negative control solution | 16.7 mg/ml | | | |
| Dose of negative control, administered orally | 2 ml/kg 33.3 mg/kg 6260 USP units/kg | | | |
| Positive control solution, administered subcutaneously | 2.4 mg/ml | 5 mg/ml | 5 mg/ml | |
| Dose of positive control, administered subcutaneously | 1 ml/kg 2.4 mg/kg 450 USP units/kg | 0.4 ml/kg 1.8 mg/kg 340 USP units/kg | 0.4 ml/kg 1.8 mg/kg 340 USP units/kg | |

Blood Sampling

The blood samples are taken by caudal incision (formulation A) or retro-orbitally (formulations B and C). A volume of 0.50 ml (formulation A) or 1 ml (formulations B and C) of blood is collected in a tube containing 3.8% sodium citrate.

The plasma is separated from the whole blood by centrifugation at 92 g for 10 min at +4° C., just after sample collection. The plasma is stored by freezing at −18° C., immediately after separation, until required for analysis.

Quantitative assay of the heparin in the rat or dog plasma is performed by a colorimetric method (SIGMA Diagnostics®, Heparin Accucolor™, Method no. CRS106). A calibration curve is plotted so that the results obtained as optical density at 405 nm can be expressed as heparinemia.

Calibration Curve

The heparin standards are prepared using a pool of plasmata taken from fasted animals in the same manner as the test samples. Four heparin standards with concentrations of 0, 0.226, 0.452 and 0.905 unit/ml are prepared.

The absorbance obtained at 405 nm for each heparin standard is plotted against the heparin concentration (units/ml). The amount of heparin in a sample can be determined from this calibration curve.

Results

The results are shown in FIGS. 1 to 3, in which the heparinemia (in units/ml), standardized to 0 at T=0, is plotted against time.

Formulation A (FIG. 1)

It is seen that the curve obtained by the oral administration of heparin incorporated in the vesicles of the invention rises to a maximum and then falls. This phenomenon is similar to that observed for the subcutaneous injection of a heparin solution, which is shown for comparison. By contrast, the oral administration of the non-encapsulated heparin solution produces no significant effect on the heparinemia of the animals.

Formulation B (FIG. 2)

It is seen that the curve obtained by the oral administration of heparin incorporated in the vesicles of the invention rises to a maximum about 1 hour after administration, and then rises. This phenomenon is similar to but more pronounced than that observed for the subcutaneous injection of the positive control heparin solution, which is shown for comparison.

Formulation C (FIG. 3)

In this case the curve obtained by the oral administration of heparin incorporated in the vesicles of the invention is seen to rise more slowly, the maximum still not having been reached 6 hours after administration. This long activity time is remarkable and considerably greater than that observed in the case of subcutaneous injection.

Also, comparison of the two curves obtained for doses I and II reveals a "dose" effect, the heparinemia obtained for dose II (18,600 USP units/kg) being appreciably greater than that corresponding to dose I (5460 USP units/kg).

1.d Study of the Administration to Dogs of the Vesicles Incorporating Heparin

A study analogous to that of the previous Example was performed on dogs with Formulation D below:

| Formulation D | |
|---|---|
| ❶ Ethoxylated lauryl alcohol (SEPPIC, Simulsol P4): | 4.0% |
| ❷ Lanolin cholesterol (FLUKA): | 3.0% |
| ❸ Sterile PBS 1x: | 10.0% |
| ❹ Heparin at 25% in sterile PBS 1x: | 40.0% |
| ❺ Soya lecithin (NATTERMANN, Phospholipon 90): | 43.0% |

Procedure

Constituents ❶, ❷ and ❸ are introduced in any order into a sterile 2 ml pill bottle and then mixed for 2 h by magnetic agitation. Total solubilization of constituent ❷ is verified by microscopic observation. Constituent ❹ is then introduced, the mixture is homogenized with a spatula and constituent ❺ is then added.

The whole is homogenized with the spatula and then left to stand overnight at 4° C.

The preparation is then dispersed at a concentration of 10% in sterile PBS 1x to give a heparin titer of 10 mg/ml in the dispersion.

Protocol

The dogs were female Beagles weighing 10 to 12 kg. The protocol was as follows:

The volume administered by esophageal tube is 3 ml/kg, i.e. 30 ml for the dogs used, corresponding to a heparin dose in the vesicles of 300 mg (30 mg/kg), i.e. 56,400 USP units per dog (5640 USP units/kg).

The animals are fasted 24 h before the treatment (water diet). Administration takes place at $T_0$, the blood samples being taken from the jugular vein at $T_0$ (before administration), $T_0+1$ h, $T_0+2$ h or $T_0+3$ h, $T_0+6$ h.

Negative control: 10 mg/ml aqueous solution of heparin; the volume administered is 30 ml, corresponding to 300 mg of heparin (30 mg/kg), i.e. 56,400 USP units per dog (5640 USP units/kg).

Positive control by subcutaneous injection; the solution is 10 mg/ml and the injection volume is 0.2 ml/kg, i.e. 2 ml for the dogs used, corresponding to a dose of 20 mg of heparin (2 mg/kg), i.e. 3800 USP units per dog (380 USP units/kg).

A size profile study of the vesicles by granulometry shows a secondary maximum around 4.5 µm which is more intense than in the case of Formulations A and B.

Results

The results are shown in FIG. 4 in the same way as for rats.

It is observed, as in the case of rats, that the curve obtained for dogs which have received heparin incorporated in the vesicles by oral administration rises under similar conditions to those observed for the solution injected subcutaneously. However, it is noted that the curve as a function of time shifts slightly towards long times when the heparin is incorporated in vesicles and administered orally. By contrast, the oral administration of a heparin solution has no influence on the heparinemia.

EXAMPLE 2

Vesicles Incorporating Calcitonin 2.a Preparation and Characterization of Vesicles Incorporating Calcitonin Similar experiments were carried out on rats with the incorporation of calcitonin, which is a peptide. In this case the main difficulty arises from the fragility of the molecule, which is very rapidly degraded in the gastrointestinal medium during the normal digestive process.

The calcitonin used is a salmon calcitonin (BACHEM H-2260) dissolved in aqueous solution in PBS 1x. The formulation and the procedure for preparation of the vesicles are similar to those used in the case of heparin (Formulation D).

| | |
|---|---|
| ❶ Ethoxylated lauryl alcohol (SEPPIC, Simulsol P4): | 04.00% |
| ❷ Lanolin cholesterol (FLUKA): | 03.00% |
| ❸ Sterile PBS 1x: | 10.00% |
| ❹ Calcitonin solution at 12,000 IU/ml in sterile PBS 1x: | 40.00% |
| ❺ Soya lecithin (NATTERMANN, Phospholipon 90): | 43.00% |

The vesicles are dispersed at a concentration of 10% in sterile PBS 1x, corresponding to a calcitonin titer of 480 IU/ml.

The granulometric profile of the vesicles shows a size distribution ranging from 50 nm to 10 µm with a main maximum centered around 0.3 µm and a relatively unpronounced secondary maximum around 3 µm. 85% of the sample has a size below 1 µm.

2.b Study of the Administration to Rats of the Vesicles Incorporating Calcitonin The study was carried out on female Wistar rats weighing 150 g, divided into groups of 4 rats. Oral administration was effected using an esophageal tube in a volume of 300 µl, corresponding to 144 IU administered per animal.

A volume of 100 µl of an aqueous solution of calcitonin with a titer of 20 IU/ml, corresponding to a dose of 2 IU of calcitonin per animal, was administered subcutaneously to a positive control group.

A volume of 300 µl of an aqueous solution of calcitonin with a titer of 240 IU/ml, corresponding to 72 IU per animal, was administered orally to a negative control group.

The animals were fasted (water diet) 24 hours before the experiment. Blood samples were taken retro-orbitally under general anesthetic at $T_0$ (before administration), $T_0+1$ h, $T_0+2$ h or $T_0+3$ h, $T_0+5$ h. 50 µl of blood are collected in microcapillary tubes containing heparin.

The blood calcium and pH are measured immediately after sample collection, directly in the microcapillary tube, by means of a CIBA-CORNING model 634 automatic analyzer to give the calcemia.

The results are summarized in FIG. 5. In the case of calcitonin incorporated in the vesicles according to the invention and administered orally, it is observed that the calcemia decreases during the first hour, to about 75% of its initial value, and then gradually increases over the next hour. This behavior is similar to that obtained for the subcutaneous injection of calcitonin in aqueous solution. By contrast, this phenomenon is not observed for the oral administration of a non-encapsulated calcitonin solution.

It can therefore be concluded that the encapsulation of calcitonin according to the invention has protected this peptide from digestion in the gastrointestinal medium and has also allowed it to pass through the intestinal mucosa.

| KEY TO THE FIGURES |
|---|
| FIG. 1 |
| -●- Heparin in solution, s.c. (450 USP units/kg) |
| -♦- Heparin in solution, p.o. (6260 USP units/kg) |
| -■- Heparin in vesicles, p.o. (6280 USP units/kg) |
| FIG. 2 |
| -●- Heparin in solution, s.c. (340 USP units/kg) |
| -■- Heparin in vesicles, p.o. (3760 USP units/kg) |
| FIG. 3 |
| -●- Heparin in solution, s.c. (340 USP units/kg) |
| -♦- Heparin in solution, p.o. (18,600 USP units/kg) |
| -■- Heparin in vesicles, p.o. (5640 USP units/kg) |
| FIG. 4 |
| -●- Heparin in solution, s.c. (380 USP units/kg) |
| -♦- Heparin in vesicles, p.o. (5640 USP units/kg) |
| -■- Heparin in solution, p.o. (5640 USP units/kg) |
| FIG. 5 |
| -♦- Negative control, aqueous solution of calcitonin, p.o. |
| -■- Calcitonin incorporated in vesicles of the invention, p.o. |
| -●- Positive control, aqueous solution of calcitonin, injected s.c. |

What is claimed is:

1. A method for oral administration of at least one active principle comprising the steps of incorporating said at least one active principle in multilamellar vesicles having a diameter of between 0.1 and 25 µm, and a lamellar liquid-crystal internal structure formed, from the center to the periphery of said vesicles, of a stack of concentric bilayers based on amphiphilic agents alternating with layers of water, aqueous solution or solution of a polar liquid, and orally administering a composition comprising said at least one active principle incorporated within said vesicles.

2. The method according to claim 1, wherein said vesicles are used as vectors for said at least one active principle, facilitating passage through the gastrointestinal barrier and/or protection from degradation.

3. The method according to claim 1, wherein said at lease one active principle comprises heparin.

4. The method according to claim 1, wherein said at least one active principle comprises a peptide.

5. The method according to claim 4, wherein said peptide is a reptile hormone.

6. The method according to claim 4, wherein said at least one active principle comprises calcitonin.

7. The method according to claim 1, wherein said vesicles contain at least one surfactant selected from the group consisting of:

hydrogenated or non-hydrogenated glycerolipids, ethoxylated or non-ethoxylated, linear or branched, saturated or mono- or polyunsaturated $C_6$ to $C_{30}$ fatty acids in the form of the acid or an alkali metal, alkaline earth metal or amine salt, ethoxylated or non-ethoxylated esters of sucrose, sorbitol, mannitol, glycerol or polyglycerol containing from 2 to 20 glycerol units, or glycol with said fatty acids, mono-, di- or triglycerides or mixtures of glycerides of said fatty acids, ethoxylated or non-ethoxlylated, linear or branched, saturated or mono- or polyunsaturated ($C_6$ to $C_{30}$ fatty alcohols, cholesterol and derivatives thereof, other derivatives with a sterol skeleton, ethoxylated or non-ethoxylated ethers of sucrose, sorbitol, mannitol, glycerol or polyglycerol containing from 2 to 20 glycerol units, or glycol with said fatty alcohols, hydrogenated or non-hydrogenated, polyethoxylated vegetable oils, polyoxyethylene/polyoxypropylene block polymers (poloxamers), polyethylene glycol hydroxystearate, sphingolipids and sphingosine derivatives, polyalkyl glucosides, ceramides, polyethylene glycol/alkyl glycol copolymers, and polyethylene glycol/polyalkylene glycol ether di-block or tri-block copolymers.

8. The method according to claim 1, wherein said vesicles have a diameter of between 0.2 and 15 µm.

9. The method according to claim 1, wherein the bilayers of said vesicles comprise at least two surfactants, including one surfactant having a hydrophilic-lipophilic balance (HLB) of between 1 and 6, and another surfactant having a hydrophilic-lipophilic balance (HLB) of between 3 and 15.

10. The method according to claim 1, wherein said vesicles also contain a polymer incorporated in said vesicles or deposited around said vesicles in the form of a coating.

11. The method according to claim 1, wherein said composition comprises a dispersion of said vesicles in a pharmaceutically acceptable medium.

12. The method according to claim 11, wherein said pharmaceutically acceptable medium comprises water or a buffered aqueous solution.

13. The method according to claim 11, wherein said pharmaceutically acceptable medium comprises a hydrophobic medium.

14. The method according to claim 11, wherein said pharmaceutical composition comprises an emulsion of said vesicles in an aqueous medium, the vesicles themselves having been previously dispersed in an oil.

15. A pharmaceutical composition for oral administration containing heparin as an active principle, incorporated in multilamellar vesicles having a diameter of between 0.1 and 25 µm, and a lamellar liquid-crystal internal structure formed, from the center to the periphery of said vesicles, of a stack of concentric bilayers based on amphiphilic agents alternating with layers of water, aqueous solution or solution of a polar liquid.

16. A pharmaceutical composition for oral administration containing calcitonin as an active principle, incorporated in multilamellar vesicles having a diameter of between 0.1 and 25 µm, and a lamellar liquid-crystal internal structure formed, from the center to the periphery of said vesicles, of a stack of concentric bilayers based on amphiphilic agents alternating with layers of water, aqueous solution or solution of a polar liquid.

17. The pharmaceutical composition according to claim 15, wherein sail vesicles have a diameter of between 0.2 and 15 µm.

18. The pharmaceutical composition according to claim 16, wherein said vesicles have a diameter of between 0.2 and 15 µm.

19. A method for oral administration of at least one active principle comprising the steps of incorporating said at least one active principle in multilamellar vesicles having a diameter of between 0.1 and 25 µm, and a lamellar liquid-crystal internal structure formed, from the center to the periphery of said vesicles, of a stack of concentric bilayers based on amphiphilic agents alternating with layers of water, aqueous solution or solution of a polar liquid, said vesicles being obtained by transformation of a lamellar liquid-crystal phase incorporating said active principle under the action of shear or mechanical stress, and orally administering a composition comprising said at least one active principle incorporated within said vesicles.

* * * * *

UNITED STATES PATENT AND TRADEMARK OFFICE
CERTIFICATE OF CORRECTION

PATENT NO. : 6,770,292 B2
DATED : August 3, 2004
INVENTOR(S) : Charles Guinez et al.

It is certified that error appears in the above-identified patent and that said Letters Patent is hereby corrected as shown below:

<u>Title page,</u>
Item [73], Assignee, change "Assignee: Capsules, Pessac (FR)" to -- Assignee: Capsulis, Pessac (FR). --.

Signed and Sealed this

Fourth Day of October, 2005

JON W. DUDAS
*Director of the United States Patent and Trademark Office*